(12) United States Patent
Sams et al.

(10) Patent No.: US 10,054,579 B2
(45) Date of Patent: Aug. 21, 2018

(54) COMMUNICATION INTERFACE CLIP FOR A HANDHELD MEDICAL DEVICE

(71) Applicant: Roche Diagnostics Operations, Inc., Indianapolis, IN (US)

(72) Inventors: Howard Sams, Carmel, IN (US); Andreas Staubert, Bad Duerkheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/098,957

(22) Filed: Apr. 14, 2016

(65) Prior Publication Data
US 2016/0238588 A1     Aug. 18, 2016

Related U.S. Application Data

(63) Continuation of application No. PCT/EP2014/072114, filed on Oct. 15, 2014.
(Continued)

(51) Int. Cl.
*G01N 33/487*     (2006.01)
*G01N 33/49*      (2006.01)
(Continued)

(52) U.S. Cl.
CPC ..... *G01N 33/48785* (2013.01); *A61B 5/0015* (2013.01); *A61B 5/0017* (2013.01);
(Continued)

(58) Field of Classification Search
CPC ....... G01N 33/48785; G01N 33/48792; G01N 33/4905; G01N 27/3273; A61B 5/0015;
(Continued)

(56) References Cited

U.S. PATENT DOCUMENTS 5,784,511 A * 7/1998 Kikuchi ............... G02B 6/3886
                                                      385/53
5,963,650 A * 10/1999 Simionescu ........... G01D 4/004
                                                      340/870.02
(Continued)

FOREIGN PATENT DOCUMENTS

JP      2009240349 A     10/2009
JP      2013511780 A      4/2013
(Continued)

OTHER PUBLICATIONS

International Search Report dated Dec. 23, 2014, in Application No. PCT/EP2014/072114, 3 pages.
(Continued)

*Primary Examiner* — Hai Phan
*Assistant Examiner* — Franklin Balseca
(74) *Attorney, Agent, or Firm* — Dinsmore & Shohl, LLP

(57) ABSTRACT

A communication interface apparatus is provided for use with a handheld medical test device. The communication interface apparatus is comprised of an attachment member configured to detachably couple to a housing of the medical test device, where the attachment member substantially overlays a rear side of the medical test device. The communication interface apparatus houses an infrared receiver, a secondary transceiver and a controller. The infrared receiver is arranged such that its input port aligns with an output port of an infrared transmitter in the medical test device when the attachment member is coupled to the medical test device.

9 Claims, 13 Drawing Sheets

Related U.S. Application Data

(60) Provisional application No. 61/891,736, filed on Oct. 16, 2013, provisional application No. 61/891,656, filed on Oct. 16, 2013.

(51) Int. Cl.
  *A61B 5/00* (2006.01)
  *A61B 5/145* (2006.01)
  *G16H 10/40* (2018.01)
  *G01N 27/327* (2006.01)
  *G16H 40/63* (2018.01)

(52) U.S. Cl.
  CPC ....... *G01N 33/48792* (2013.01); *G16H 10/40* (2018.01); *A61B 5/14532* (2013.01); *A61B 5/14546* (2013.01); *A61B 2560/045* (2013.01); *A61B 2560/0431* (2013.01); *A61B 2562/0295* (2013.01); *G01N 27/3273* (2013.01); *G01N 33/4905* (2013.01); *G16H 40/63* (2018.01)

(58) Field of Classification Search
  CPC .............. A61B 5/0017; A61B 5/14532; A61B 5/14546; A61B 2560/0431; A61B 2560/045; A61B 2562/0295; G06F 19/366; G06F 19/3406; G16H 10/40; G16H 40/63; H04Q 9/00; H04Q 2209/00; H04Q 2209/40; H04Q 2209/883
  See application file for complete search history.

(56) References Cited

U.S. PATENT DOCUMENTS

| | | | |
|---|---|---|---|
| 2009/0085768 A1* | 4/2009 | Patel | A61B 5/14532 340/870.05 |
| 2011/0184491 A1 | 7/2011 | Kivi | |
| 2011/0256024 A1* | 10/2011 | Cole | A61B 5/0022 422/68.1 |
| 2012/0094600 A1* | 4/2012 | DelloStritto | A61B 5/0015 455/41.2 |
| 2012/0095312 A1 | 4/2012 | Ramey et al. | |
| 2013/0273983 A1* | 10/2013 | Hsu | H05K 5/0086 455/575.1 |

FOREIGN PATENT DOCUMENTS

| | | |
|---|---|---|
| WO | 2004090503 A2 | 10/2004 |
| WO | 2011094075 A2 | 8/2011 |

OTHER PUBLICATIONS

First Chinese Office Action dated Dec. 13, 2017, pertaining to Chinese Patent Application No. 201480056812.6 filed Oct. 15, 2014, English Translation.

Japanese Office Action dated Mar. 5, 2018, pertaining to Japanese Patent Application No. 2016-523914—with Translation.

* cited by examiner

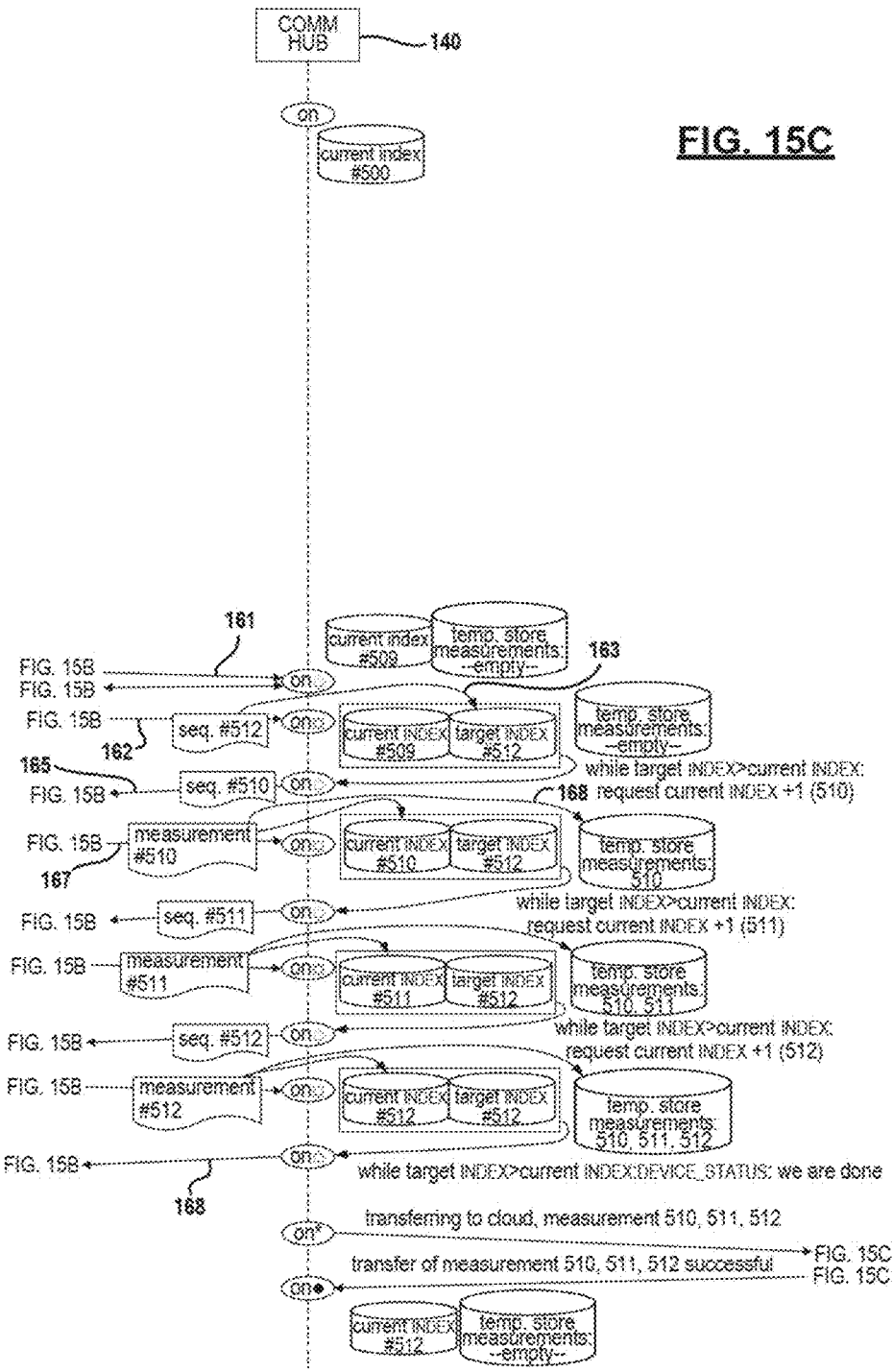

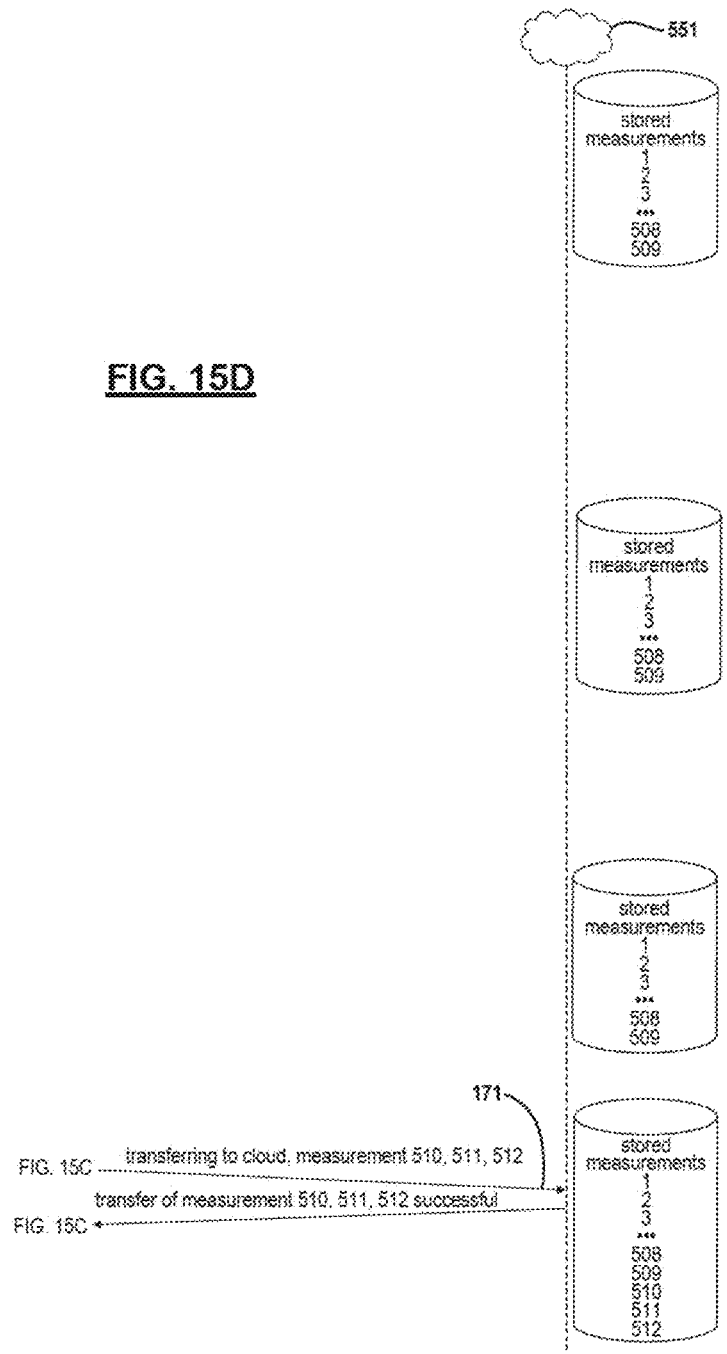

ΩCOMMUNICATION INTERFACE CLIP FOR A HANDHELD MEDICAL DEVICE

FIELD

The present disclosure relates to a communication interface apparatus for a handheld medical device having an infrared communication link.

BACKGROUND

Oral anticoagulation therapy is necessary if a patient has an artificial heart valve, or if they are affected by atrial fibrillation or thrombotic diseases. For patients receiving oral anticoagulation therapy with warfarin, it is important that the dosage is exactly right. The patient's level of coagulation requires regular monitoring, as patients react differently to warfarin, and several factors may interfere with the drugs such as food and other medications. The International Normalized Ratio (INR) is a standardized method of measuring the rate at which blood coagulates. It is very important that patients stay within their target INR range. If a patient's INR is too low, the risk of blood clots increases. If a patient's INR is too high, the risk of internal bleeding increases.

Properly trained patients and/or caregivers are capable of performing reliable INR testing using the patient self-testing model. Handheld blood clot testing meters have enabled patients to implement self-testing. For these patients, self-testing is cost effective and leads to outcomes at least as good as standard INR testing in a specialized clinic. Handheld blood clot testing meters are a sub-category of handheld medical test devices. Other handheld medical test devices are known, like handheld blood glucose meters, lipid testing meters or cardiac marker testing meters.

Despite the success of self-testing, it remains inconvenient for healthcare providers to retrieve test results from the meters used by patients to self-test. An innovative solution is required to address the growing demand from patients for wireless connectivity. Thus, there is a need for means to seamlessly transfer INR or other test results from a handheld medical device wirelessly locally to a communication hub and/or remotely to a server associated with a healthcare provider.

This section provides background information related to the present disclosure which is not necessarily prior art.

SUMMARY

This section provides a general summary of the disclosure, and is not a comprehensive disclosure of its full scope or all of its features.

A communication interface apparatus is provided for use with a handheld medical test device. The communication interface apparatus includes an attachment member that is configured to detachably couple to a housing of the medical test device, where the attachment member substantially overlays a rear side of the medical test device. In an embodiment, the attachment member overlays at least 50%, typically at least 66%, more typically at least 75%, more typically at least 80%, more typically at least 90%, of the area of the rear side of the medical test device. The communication interface apparatus further includes: an infrared receiver/transceiver, a secondary transceiver, a controller and a power source. The infrared receiver resides in an enclosure of the attachment member and is configured to receive data wirelessly in accordance with a first communication protocol from the infrared transmitter of the medical test device, such that an input port of the infrared receiver aligns with an output port of the infrared transmitter in the medical test device when the attachment member is coupled to the medical test device. The secondary transceiver resides in the enclosure of the attachment member and is configured to transmit data wirelessly in accordance with a wireless second communication protocol, where the first communication protocol differs from the wireless second communication protocol. The controller also resides in an enclosure of the attachment member and operates in a low power mode. The controller periodically transitions from the low power mode to a normal mode and interacts with the infrared receiver in the normal mode to receive data from the medical test device, where the communication interface apparatus consumes more electric power in the normal mode than the low power mode.

In one aspect, the attachment member is further defined by a top edge, a bottom edge and two opposing side edges extending along a planar body between the top edge and the bottom edge. Two clip portions extend outwardly from an opposing side edge of the attachment member and are configured to clip to an outer side surface of the medical test device. More specifically, the housing of the medical test device is formed by an upper shell and a lower shell coupled together and forms a groove where an edge of the upper shell abuts against an edge of the lower shell. Each clip portion of the attachment member includes a tongue that is received in the groove to create a tongue-and-groove joint when the attachment member is coupled to the medical test device.

In another aspect, the attachment member may further include an overhang portion extending outwardly from a top edge of the attachment member and overlays a portion of a top side of the medical test device when the attachment member is coupled to the medical test device, such that the overhang portion encases the infrared receiver and the input port of the infrared receiver faces the top side of the medical test device. A visual indicator may reside in the overhang portion and be electrically connected to the controller, wherein the visual indicator is illuminated while data is transmitted between the meter and the communication interface apparatus.

In yet another aspect, the planar body of the attachment member defines a longitudinal axis extending between the top edge and the bottom edge of the planar body, and the planar body is shaped such that the longitudinal axis is parallel with a horizontal surface upon which the attachment member rests and while the attachment member is coupled to the medical test device.

Additionally, the communication interface further includes a power switch electrically interconnected between the power source and the controller, wherein the power switch is accessible outside of the enclosure to selectively power on and off the communication interface apparatus.

In some embodiments, the communication interface apparatus is configured to communicate data wirelessly via the secondary transceiver to a communication hub, where the communication hub can be configured to plug into a AC power source. In other embodiments, the communication hub is further defined as a mobile phone. In some cases, the communication interface apparatus may be packaged together with a communication hub as a kit.

In operation, the communication interface apparatus operates in a low power mode and periodically transitions from the low power mode to a normal mode that consumes more electric power than the low power mode. Upon transitioning to the normal mode, the controller interacts with the infrared receiver/transceiver to query the handheld medical device, e.g., a blood clot testing meter. Upon failing to receive a response to the query from the handheld medical device, the communication interface apparatus transitions back to the low power mode. Upon receiving a response to the query from the handheld medical device, the controller interacts with the infrared receiver/transceiver to transmit a request for test results to the handheld medical device. In response to receiving a test result from the handheld medical device, the controller interacts with the secondary transceiver to transmit the test result to the communication hub.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 15C is a sequence diagram depicting an example communication protocol employed by the communication interface apparatus;

FIG. 15D is a sequence diagram depicting an example communication protocol employed by the communication interface apparatus.

Figure 1:
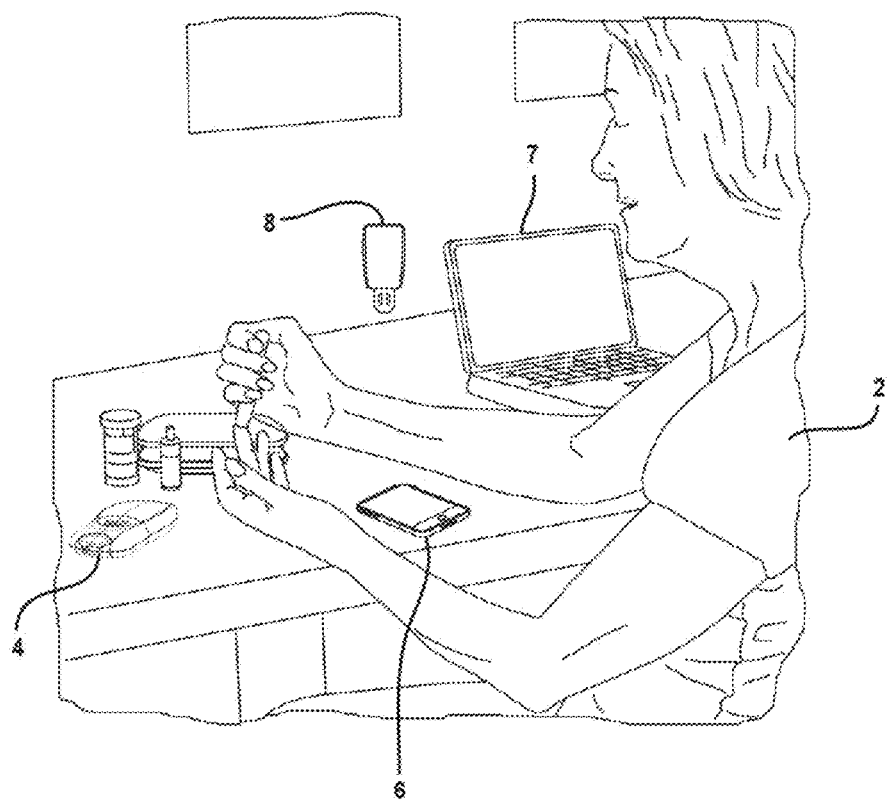
FIG. 1 is a diagram of a patient administering a self-test.

Corresponding reference numerals indicate corresponding parts throughout the several views of the drawings. Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

Example embodiments will now be described more fully with reference to the accompanying drawings.

FIG. 1 illustrates a patient 2 administering a self-test using a handheld medical device 4. The patient is shown obtaining a blood sample for depositing on a test strip. The test strip is inserted in a strip port of the medical device 4 and a measurement result is determined by the medical device 4. In one embodiment of the instant disclosure, the test strip is inserted in the strip port of the medical device 4 prior to applying the blood sample to the test strip. The medical device 4 can have an integrated heating element to warm the test strip to a pre-determined temperature. When this warm-up process is complete, the medical device 4 can provide an indicator to the operator that he/she can now apply a blood sample to the test strip. The indicator can be, for example, audible, such as a beep, or visual, such as a displayed icon on a screen, or light, or both. In yet another embodiment, the blood sample could be applied to the test strip before or simultaneously with insertion of the test strip into the strip port of the medical device 4.

It is desirable that the measurement results obtained by the medical device 4 be transferred seamlessly and typically without further patient intervention to another local computing device, such as a mobile phone 6, tablet or other capable mobile computing device, a laptop computer 7, or a communication hub 8. A communication interface apparatus to facilitate such wireless connectivity is further described below.

Figure 2A:
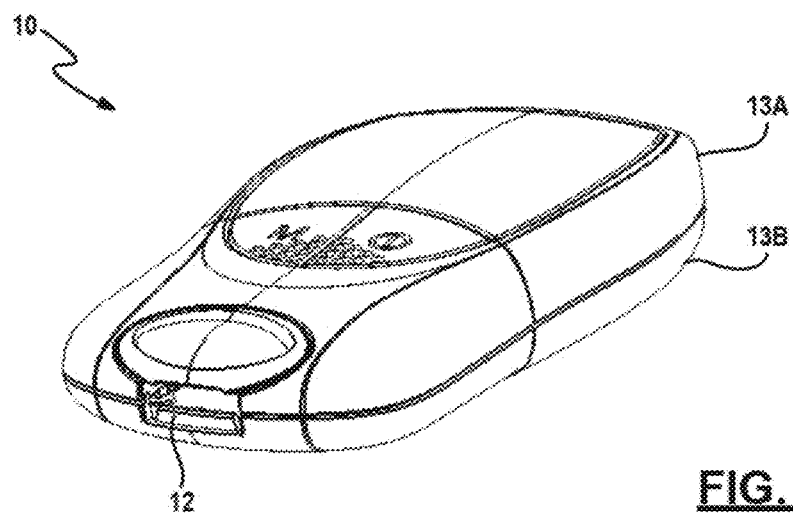
FIG. 2A is a perspective view of an example medical test device.
Figure 2B:
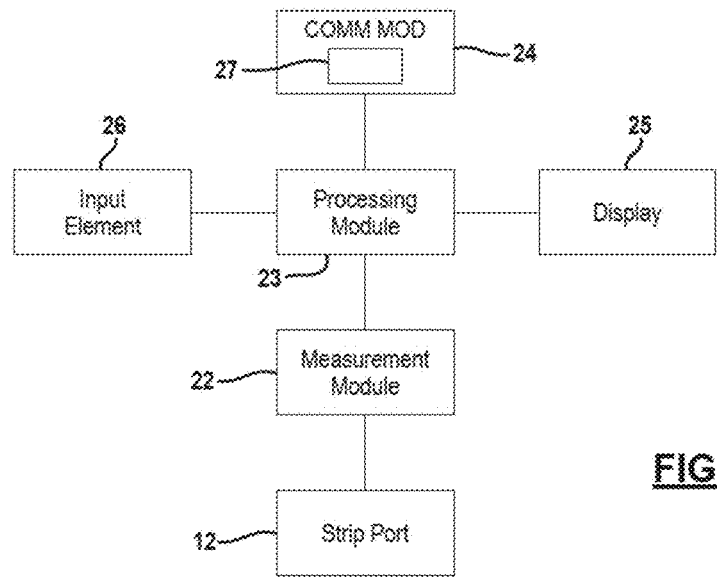
FIG. 2B is a block diagram depicting the electronic components of the medical test device.

FIG. 2A and FIG. 2B further depict an example handheld medical test device 10. In an example embodiment, the medical test device 10 is further defined as a blood clot testing meter which may be used by patients to measure their international normalized ratio (INR) or similar metrics indicative of the clotting tendency or rate at which blood clots. The CoaguChek® XS blood clot testing monitor is an example meter commercially available from Roche Diagnostics. The CoaguChek® XS system (CoaguChek® XS meter and CoaguChek® XS PT Test strips) quantitatively determines prothrombin time ("PT"), using capillary blood or whole blood from a vein (nonanticoagulated venous whole blood). The system is suited to monitor coagulation values in people who are taking oral anticoagulation medication such as warfarin (vitamin K antagonists, VKAs). The CoaguChek® XS PT Test contains a lyophilized reagent. The reactive components of this reagent consist of thromboplastin and a peptide substrate. When a sample is applied, thromboplastin activates coagulation, which leads to the formation of thrombin. At the same time the meter starts to measure the time. The enzyme thrombin cleaves the peptide substrate, generating an electrochemical signal. Depending on the time elapsed when it first appears, this signal is then converted by means of an algorithm into customary coagulation units (INR, % Quick, seconds) and the result is displayed. While reference is made throughout this application to a blood clot testing meter, the broader aspects of this disclosure pertain to other types of handheld medical devices, such as meters for monitoring blood glucose, lipids, cardiac markers or the like, individually and/or in combination.

With reference to FIG. 2B, the medical test device 10 is comprised generally of a measurement module 22, a processing module 23 and a communication module (COM MOD) 24. During operation, the measurement module 22 cooperatively interacts with a test strip inserted into a strip port 12 to determine and display coagulation values, i.e., prothrombin time of a nonanticoagulated venous whole blood sample applied to a test strip. The medical test device 10 can display test results in units equivalent to laboratory plasma measurements, i.e., INR, combination of INR/seconds, or combination of INR/% Quick. The measurement module 22 may include calibration information for the test strips being read by the medical test device 10. Each box of test strips has its own code chip for insertion into the medical test device 10. The code chip contains lot-specific information about its test strips, such as the expiration date and calibration data. Optional liquid controls for the system are also available.

As used herein, the term "module" may refer to, be part of, or include an application Specific Integrated Circuit (ASIC); an electronic circuit; a combinational logic circuit; a field programmable gate array (FPGA); a computer processor that executes computer readable instructions; other suitable components that provide the described functionality; or a combination of some or all of the above.

The processing module 23 is configured to receive test results that can be customary coagulation units (e.g., INR, INR/seconds, or INR/% Quick) from the measurement module 22 and automatically store the measurement data for subsequent processing. In the example embodiment, each test result (patient test or control) is tagged with identifying information. Identifying information may include but is not limited to a date/time stamp for when the measure was taken, patient ID (and operator ID activated), a serial number for the meter and other information pertaining to the test strip, i.e., lot code, test type like prothrombin time (PT). Of note, each test result measure is also tagged with a unique sequence number assigned by the meter or medical test device 10. In one embodiment, a counter is incremented each time a measurement is taken and the value of the counter is assigned to the test result. The sequence number may be used to retrieve data from the meter as is further described below. Once tagged, the test result is automatically stored in a memory of the medical test device 10. Additionally, the test result can be displayed by the processing module 23 on a display 25. The user interacts with the medical test device 10 using various interface components/interface elements 26 (e.g., buttons, switches, a speaker, a microphone, USB port, etc.), which are also interfaced with the processing module 23. In an exemplary embodiment, the processing module 23 is implemented by a microprocessor and one or more volatile and/or non-volatile memories.

The processing module 23 is also interfaced with the communication module (COM MOD) 24. In an exemplary embodiment, the communication module 24 includes an infrared transceiver 27. The infrared transceiver 27 operates to communicate the test result(s) and other data wirelessly via a serial data link to other devices physically separated from the medical test device 10. It is understood that the communication module 24 may further include its own microcontroller, voltage control circuits, etc. Although a few primary components of the medical test device 10 are discussed herein, it is readily understood that other components (e.g., power source) may be needed to implement the medical test device 10.

Figure 3:
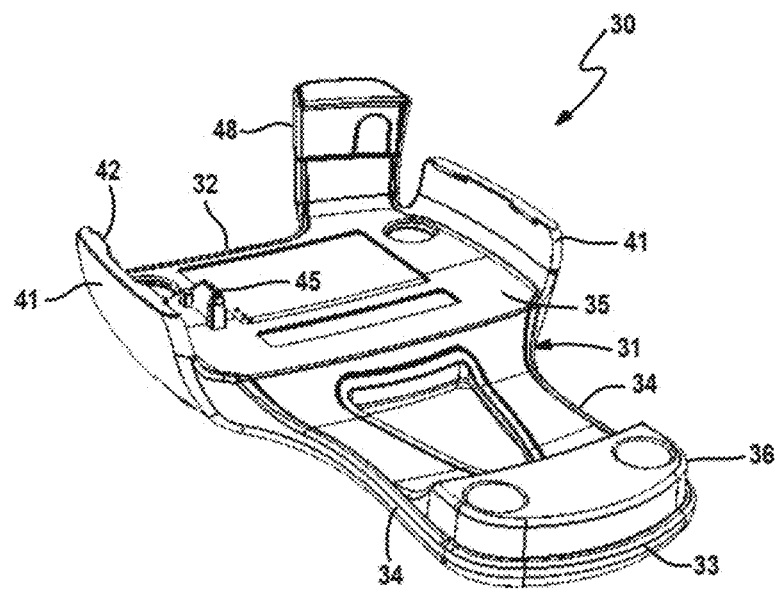
FIG. 3 is a perspective view of a communication interface apparatus for use with the medical test device.
Figure 4:
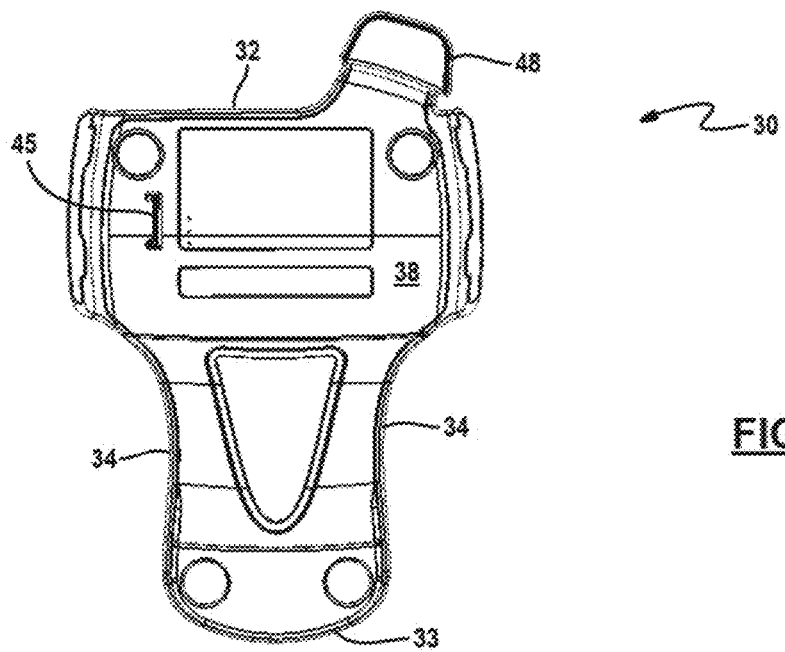
FIG. 4 is a front view of the communication interface apparatus.
Figure 5:
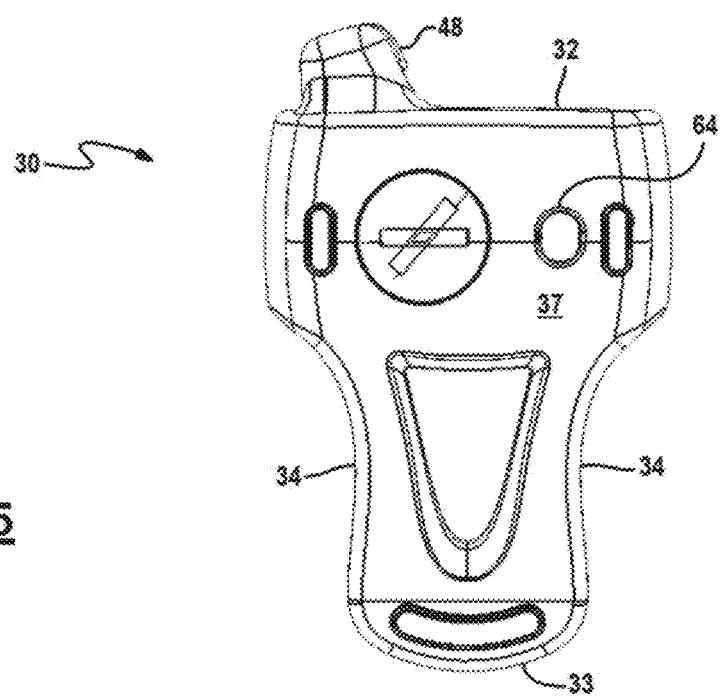
FIG. 5 is a rear view of the communication interface apparatus.
Figure 7:
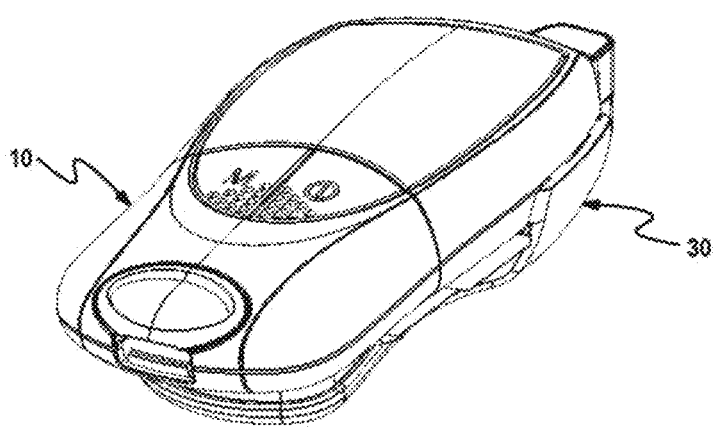
FIG. 7 is a perspective view of the communication interface apparatus coupled to the medical test device.
Figure 8:
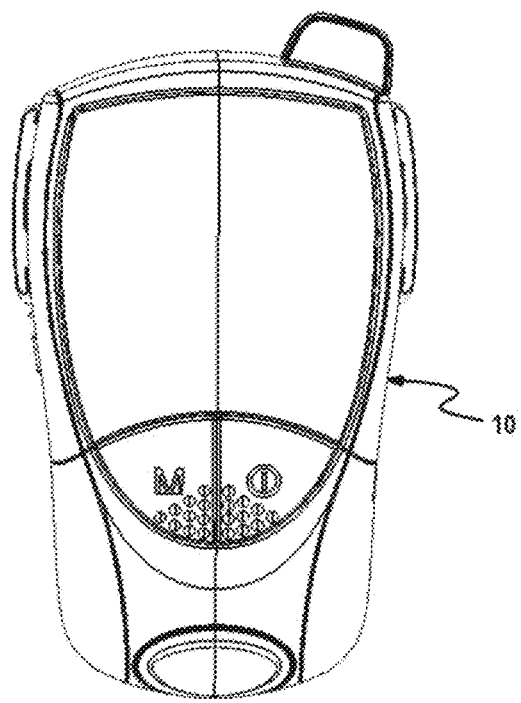
FIG. 8 is a front view of the communication interface apparatus coupled to the medical test device.
Figure 9:
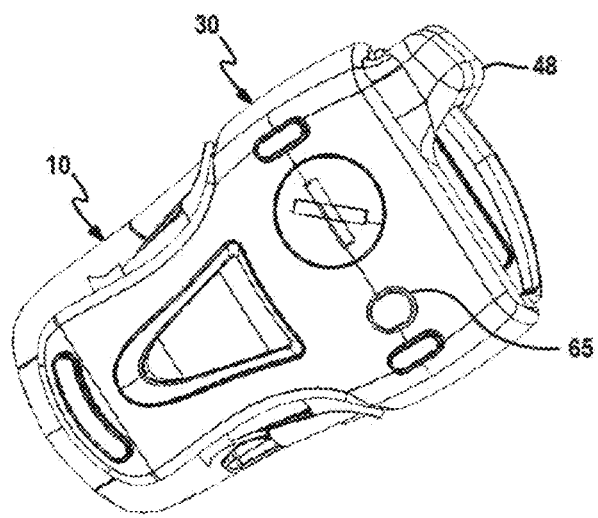
FIG. 9 is a rear view of the communication interface apparatus coupled to the medical test device.

FIGS. 3-5 depict an example communication interface apparatus 30 designed for use with the handheld medical test device 10. The communication interface apparatus 30 is comprised primarily of an attachment member 31 that detachably couples to the housing of the medical test device 10. The attachment member 31 has a planar body that defines a top edge 32, a bottom edge 33 and two opposing side edges 34, and provides at least one enclosure 35 for housing various electronic components as will be further described below.

Figure 10:
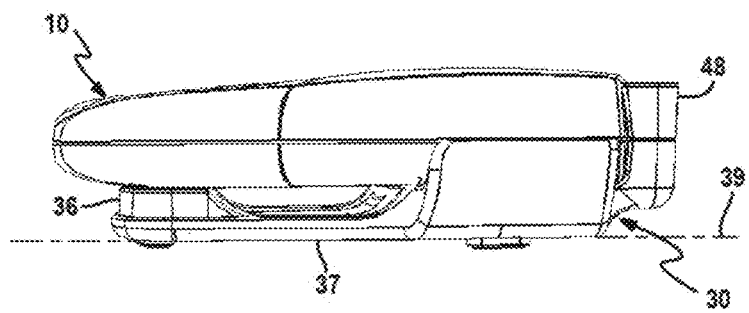
FIG. 10 is a side view of the communication interface apparatus coupled to the medical test device.
Figure 11:
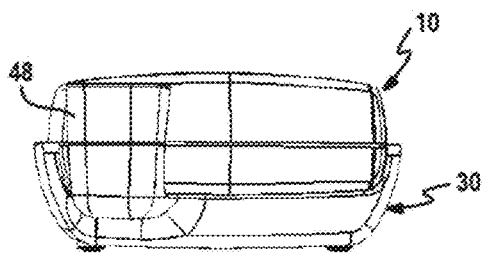
FIG. 11 is a top view of the communication interface apparatus coupled to the medical test device.

The shape of the attachment member 31 may take different forms while meeting a few basic requirements. The attachment member 31 is designed so as not to overlap or overlay any buttons, switches, displays or other user interface components/input elements of the medical test device 10, including buttons commonly found on top of a meter. The attachment member 31 should also provide sufficient clearance from the strip port 12 (FIG. 2A) of the medical test device 10 to ensure operability. In addition, the attachment member 31 is typically configured to lay flat on a horizontal surface when coupled to the medical test device 10 as best seen in FIG. 10. That is, the planar body of the attachment member 31 defines a longitudinal axis 39 extending between the top edge 32 and the bottom edge 33 of the planar body and the planar body is shaped such that the longitudinal axis 39 is parallel with a horizontal surface upon which the attachment member 31 rests while the attachment member 31 is coupled to the medical test device 10. In the example embodiment, the attachment member 31 includes a raised portion 36 proximate to the bottom edge 33, where the raised portion 36 has a depth substantially the same as the depth of the enclosure 35 and thereby forms a substantially planar rear surface 37 for level placement on horizontal surfaces such as tables, desks and the like.

Figure 12:
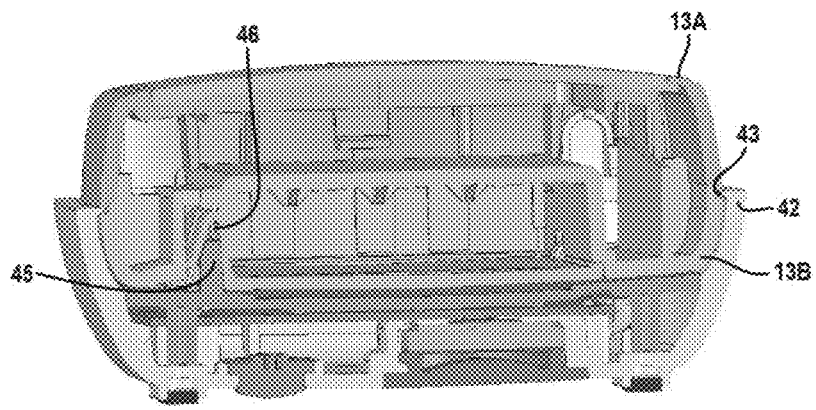
FIG. 12 is a cross-sectional view of the communication interface apparatus coupled to the medical test device.

In the example embodiment, the attachment member 31 is configured to clip to outer side surfaces of the medical test device 10. More specifically, the attachment member 31 includes two clip portions 41. Clip portions 41 extend outwardly from opposing side edges 34 of the attachment member 31. Each clip portion 41 further includes a tongue 42 that is received in a side surface of the medical test device 10. In this example, the housing of the medical test device 10 is formed by an upper shell and a lower shell coupled together. A groove 43 is formed in the housing where an edge of the upper shell abuts against an edge of the lower shell and the tongues 42 are sized to fit into the groove 43 as seen in FIG. 12. When clipped together, the tongue 42 and the groove 43 form a tongue-and-groove joint, which couples the attachment member 31 along both side surfaces of the medical test device 10. While a particular clip mechanism has been set forth, it is envisioned that other types of fastening mechanisms, such as screws, a hook and loop fastener, magnets, etc., also fall within the scope of this disclosure.

One or more protrusions 45 help to further secure the attachment member 31 to the medical test device 10. The protrusions 45 extend outwardly from a front surface 38 of the attachment member 31. Each protrusion 45 is in turn received into a recess 46 formed in a rear surface of the medical test device 10 as best seen in FIG. 12. In the example embodiment, the recess 46 is part of a latch that opens and closes a panel enclosing a battery compartment. In this way, the design of a pre-existing medical test device does not need to be modified to accommodate the communication interface apparatus 30.

The communication interface apparatus 30 is intended to enhance the wireless connectivity of the medical test device 10 by interfacing the medical test device 10 to another type of wireless data link. To enable such an interface, the communication interface apparatus 30 includes an infrared receiver (or transceiver) whose input port must align with an output port of an infrared transmitter (or transceiver) residing in the medical test device 10 while the attachment member 31 is coupled to the medical test device 10. In the example embodiment, the output port of the infrared transmitter is embedded in the top side of the medical test device 10. Consequently, the attachment member 31 includes an overhang portion 48 that extends outwardly from a top edge of the attachment member 31. The overhang portion 48 encases the infrared receiver and overlays a portion of the top side of the medical test device 10. In this way, the input port of the infrared receiver aligns with the output port of the infrared transmitter found in the medical test device 10. It is readily understood that the infrared transmitter may have different placements in other devices and thus the shape of the attachment member 31 can be altered to accommodate alignment between the infrared components.

Figure 6:
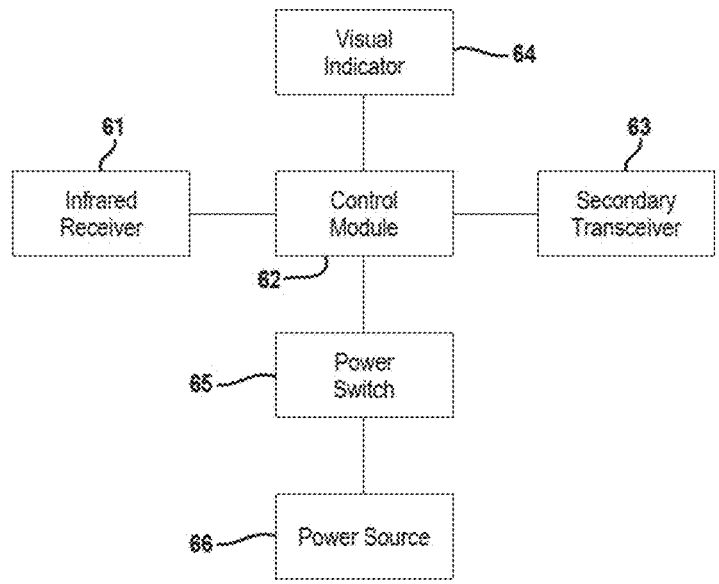
FIG. 6 is a block diagram of the electronic components of the communication interface apparatus.

FIG. 6 illustrates the electronic components associated with the communication interface apparatus 30. An infrared receiver 61 is disposed in the overhang portion 48 of the attachment member 31 as described above. The infrared receiver (or transceiver) is configured to interface with an infrared transmitter residing in the medical test device. That is, the infrared receiver 61 receives and processes data sent wirelessly in accordance with a first communication protocol, where a suitable communication protocol ensures the integrity and privacy of the transported data over a serial infrared communication link.

Figure 13:
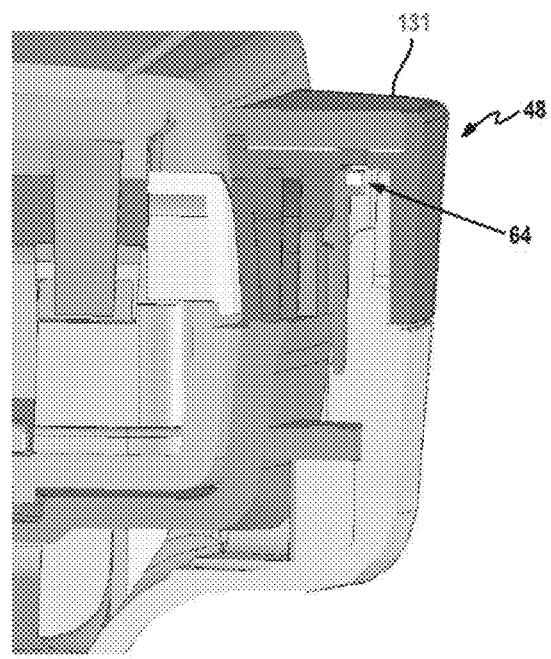
FIG. 13 is a fragmentary cross-sectional view of the overhang portion of the communication interface apparatus.

To provide visual feedback regarding the progress of any data communication, the overhang portion 48 may also house one or more visual indictors 64 as seen in FIG. 13. In an example embodiment, the visual indicator 64 is implemented by a light emitting diode mounted on a circuit board. At least a portion 131 of the overhang portion 48 is comprised of a transparent material, which emits the light from the visual indicator 64. In other embodiments, the visual indicator 64 may be disposed elsewhere on the attachment member 31.

A controller or control module 62 is housed in the primary enclosure 35 provided by the attachment member 31. The controller 62 receives data from the infrared receiver 61 and interacts with a secondary wireless transceiver 63 to transmit the data wirelessly to a local computing device. Conversely, the controller 62 may also receive data from the secondary wireless transceiver 63 and interact with the infrared receiver 61 to transmit the data wirelessly to the medical test device 10. In such an embodiment, the infrared receiver 61 is also able to work as an infrared transceiver to transmit data via infrared connection to the medical test device 10. In one embodiment, the control module 62 is implemented by a single processor. In other embodiments, the control module 62 is comprised of two processors; one processor implements application functions (e.g., converting data between different communication protocols) and a second processor is dedicated to implementing the communication protocol used by the secondary wireless transceiver 63.

In the example embodiment, the secondary transceiver 63 transmits and receives data in accordance with the IEEE 802.15 standard (i.e., the Bluetooth or Bluetooth Low Energy wireless technology standard). In other embodiments, it is envisioned that the secondary transceiver 63 may transmit and receive data in accordance with other communication protocols operating in the RF spectrum (e.g., IEEE 802.11 standard) or operate in other frequency spectrums, such as cellular or satellite technology. In any case, the secondary transceiver 63 communicates data via a wireless data link to a computing device spatially separated from the communication interface apparatus 30.

A power source 66, such as a battery, is also housed in the primary enclosure 35 provided by the attachment member 31. In one embodiment, the power source 66 provides power to the control module 62, which in turn powers the other electronic components. An on/off (power) switch 65 is electrically interconnected between the control module 62 and the power source 66. The on/off or power switch 65 enables a user to power on and off the communication interface apparatus 30 in order to conserve battery power. In the example embodiment, the on/off or power switch 65 may be implemented by a slide type switch accessible on the rear of the communication interface apparatus 30. While the primary electronic components have been discussed in relation to FIG. 6, it is understood that other electronic components may be employed by the communication interface apparatus 30.

FIGS. 7-11 further illustrate the communication interface apparatus 30 when it is coupled to the medical test device 10. Of note, the planar body of the attachment member 31 substantially overlays a rear side of the medical test device 10 but does not otherwise overlap or obstruct other portions of the medical test device 10 including its display, buttons or strip port.

Figure 14:
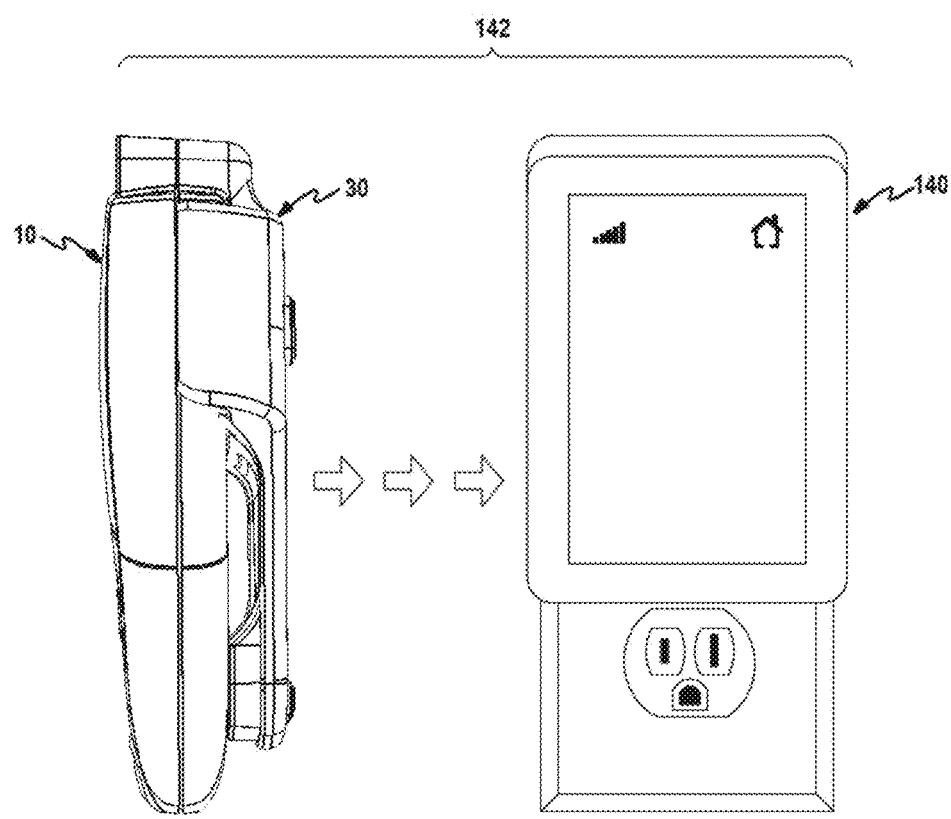
FIG. 14 is a diagram depicting a communication interface apparatus in data communication with an example communication hub.
Figure 15A:
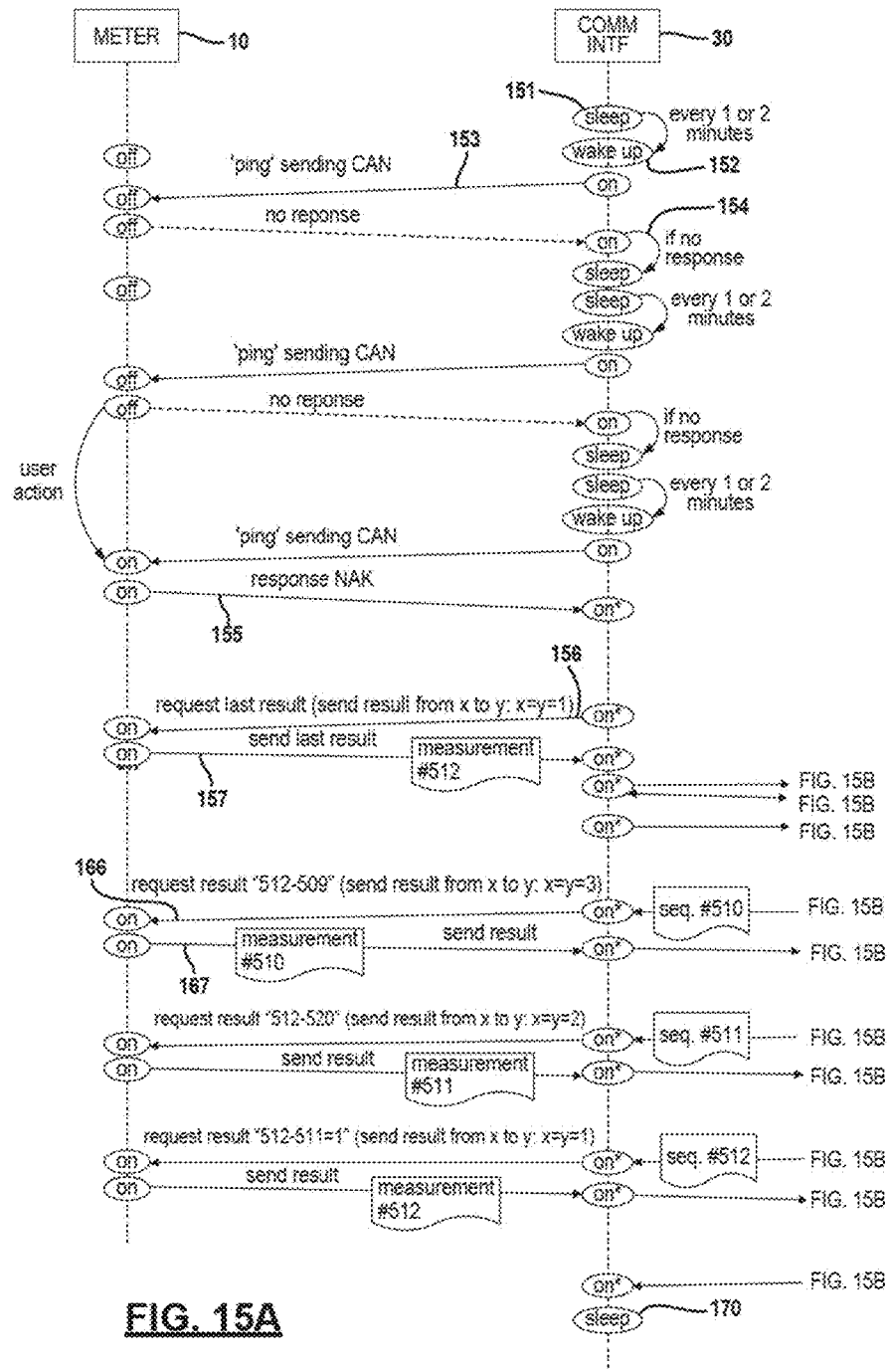
FIG. 15A is a sequence diagram depicting an example communication protocol employed by the communication interface apparatus.
Figure 15B:
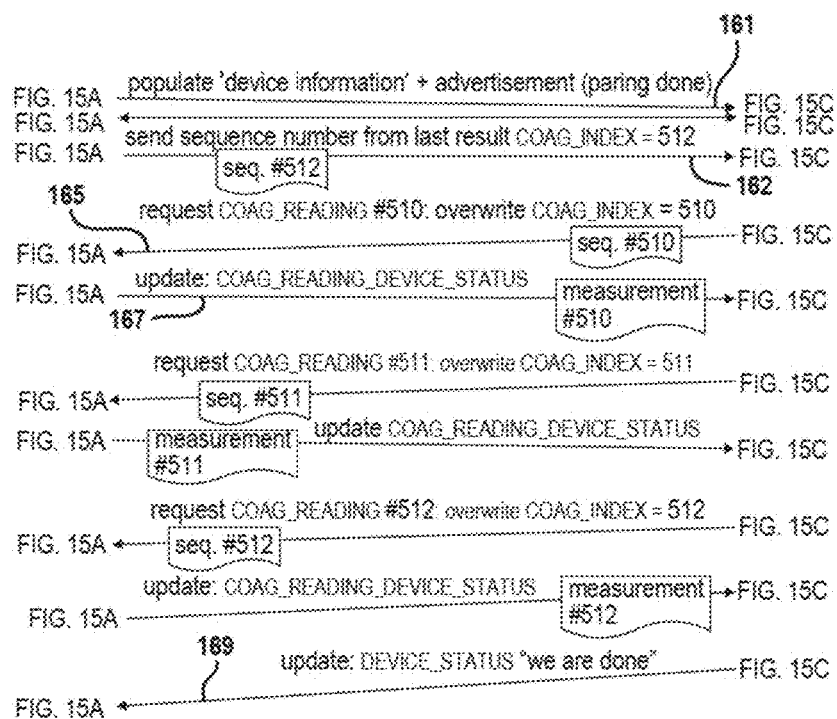
FIG. 15B is a sequence diagram depicting an example communication protocol employed by the communication interface apparatus.

FIG. 14 depicts the communication interface apparatus 30 in data communication with an example communication hub 140 while being coupled to the medical test device 10. The communication hub 140 is configured to transmit and receive requests to and from the communication interface apparatus 30 over a wireless data link. Data may be transmitted in accordance with the IEEE 802.15 standard although other wireless technology is also contemplated as noted above. The communication hub 140 can in turn process and/or store test results received from the communication interface apparatus 30. More importantly, the communication hub 140 is typically designed to relay the test results to a remote server (not shown). In an example embodiment, the communication hub 140 is a 2Net™ Hub commercially available from Qualcomm Life. In this case, it is envisioned that the communication interface apparatus 30 and the communication hub 140 may be sold together as a kit 142 with or without the medical device. In accordance with one example embodiment of the disclosure, the kit 142 can be the CoaguChek® XS mPOC Kit (Roche Diagnostics). In another example embodiment, the communication hub 140 may be an app on a mobile phone, tablet or other capable mobile computing device, and/or laptop computer. For example, the communication hub 140 can also be the CoaguChek® XS mPOC App (Roche Diagnostics). Other implementations for the communication hub 140 are also contemplated by this disclosure.

An example communication protocol between these devices is further described in relation to FIGS. 15A-15D. To begin, a user slides the on/off switch of the communication interface apparatus 30 from an 'off' to 'on' position, thereby powering it on. Initially, the communication interface apparatus 30 may enter a low power mode (i.e., sleep mode) to conserve power as indicated at 151. In a low power mode, the controller may be active but other components, such as transceivers, are powered down. At periodic time intervals (e.g., every 1 minute), the communication interface apparatus 30 transitions from the low power mode to a normal mode and begins interacting with the medical device or meter 10. More specifically, the communication interface apparatus 30 wakes-up at 152 and pings the meter 10 at 153 (i.e., sends a wake-up request). In some instances, the meter 10 is powered down and thus does not respond to the wake-up request. After failing to receive a response (e.g., within 5 seconds), the communication interface apparatus 30 returns to sleep mode as indicated at 154. This process is repeated until an acknowledgement is received from the meter 10 or the communication interface apparatus 30 is powered down.

When the meter 10 is powered on, it will send an acknowledgement message at 155 in response to the wake-up request received from the communication interface apparatus 30. The communication interface apparatus 30 can then initiate interaction with the meter 10 to obtain available test results. More specifically, the communication interface apparatus 30 sends a request to send last test result at 156. In response to the last result request, the meter 10 sends the last test result at 157 to the communication interface apparatus 30. Each test result is tagged with a unique sequence number (e.g., measurement #512 in FIGS. 15A-15D), which is included in the data sent to the communication interface apparatus 30. During the transmission from the meter 10 to the communication interface apparatus 30, the visual indicator 64 on the communication interface apparatus 30 will be illuminated in a particular manner (e.g., flashing green) indicating data is being transmitted between the meter 10 and the communication interface apparatus 30. In some instances, the data transfer may be interrupted, for example if the patient initiates a new measurement using the meter 10. In this case, the last test result is not sent by the meter 10 and the communication interface apparatus 30 returns to sleep mode after failing to receive a test result.

In the example embodiment, the communication interface apparatus 30 is not designed to store test results received from the meter 10. Rather, immediately upon receipt of test results, the communication interface apparatus 30 relays the test result to the communication hub 140 without any involvement by the user. The communication interface apparatus 30 first confirms availability of the communication hub 140 (or otherwise pairs therewith) at 161. During the pairing process, the communication interface apparatus 30 and the communication hub 140 may exchange an authentication token (e.g., a secret PIN). In the event that a data link cannot be established or the communication hub 140 is otherwise unavailable, the communication interface apparatus 30 would return to sleep mode.

At 162, the communication interface apparatus 30 transmits the last test result, including its unique sequence number, to the communication hub 140. During the transmission from the communication interface apparatus 30 to the communication hub 140, the visual indicator 64 on the communication interface apparatus 30 continues to be illuminated in the same manner as noted above (e.g., flashing green).

Test results can be stored at the communication hub 140. Upon receipt of the last test result, the sequence number for the incoming test result (i.e., #512) is compared at 163 to the sequence number for the test result last received and stored (i.e., #509) by the communication hub 140. When the sequence numbers match, the test results stored at the communication hub 140 are in synch with the test results stored on the meter 10. The communication hub 140 sends a reply at 169 to the communication interface apparatus 30 indicating that data transfer is complete. In response to such reply, the communication interface apparatus 30 returns to a sleep mode as indicated at 170. Prior to entering a sleep mode, the visual indicator 64 may be illuminated in a different manner to indicate that all data has been successfully transmitted to the communication hub 140. For example, the visual indicator 64 may be illuminated steady or flashing blue to indicate a successful transmission. Other means for varying the illumination pattern (e.g., solid vs. flashing) are also contemplated by this disclosure. Additionally, the illumination pattern for the visual indicator 64 may be further varied in order to indicate other functions such as successful pairing between devices, startup procedure in progress or weak battery.

On the other hand, when the sequence numbers do not match, the test results stored at the communication hub 140 are not in synch with the test results stored on the meter 10. In this case, the communication hub 140 sends a request for additional test results to the communication interface apparatus 30 at 165. In the example embodiment, the request for additional test result includes a sequence number for the test result being requested, where the value of the sequence number is the sequence number of the test result last received by the communication hub 140 incremented by one (e.g., #510 in FIG. 12). The request for additional test result is forwarded on at 166 to the meter 10.

In response to the request for additional test results, the meter 10 retrieves the applicable test result using the specified sequence number (i.e., #510) and sends the test result via the communication interface apparatus 30 to the communication hub 140 as indicated at 167. Upon receipt of the additional test result at the communication hub 140, the sequence number for the incoming test result (i.e., #510) is again compared at 168 to the sequence number for the test result last received (i.e., #512) and stored by the communication hub 140. The process described above is repeated as shown until the sequence number for the incoming test result matches the sequence number for the test result last received and stored by the communication hub 140. In this way, the test results are transmitted in a defined order so that even if data transmission is interrupted, transmission can be completed at a later time without missing a test result.

When the sequence numbers match, the test results stored at the communication hub 140 are in synch with the test results stored on the meter 10 and the communication hub 140 sends a reply to the communication interface apparatus 30 indicating that data transfer is complete. Again, the visual indicator 64 may be illuminated in a manner to indicate that all data has been successfully transmitted to the communication hub 140. The successful data transmission may also trigger the transfer of the data by the communication hub 140 to a remote server 551, for example associated with a healthcare provider. See, FIG. 15D at 171. It is to be understood that only the relevant steps are discussed in relation to FIGS. 15A-15D, but that other software-implemented instructions may be needed to transmit data between the devices.

Figure 16:
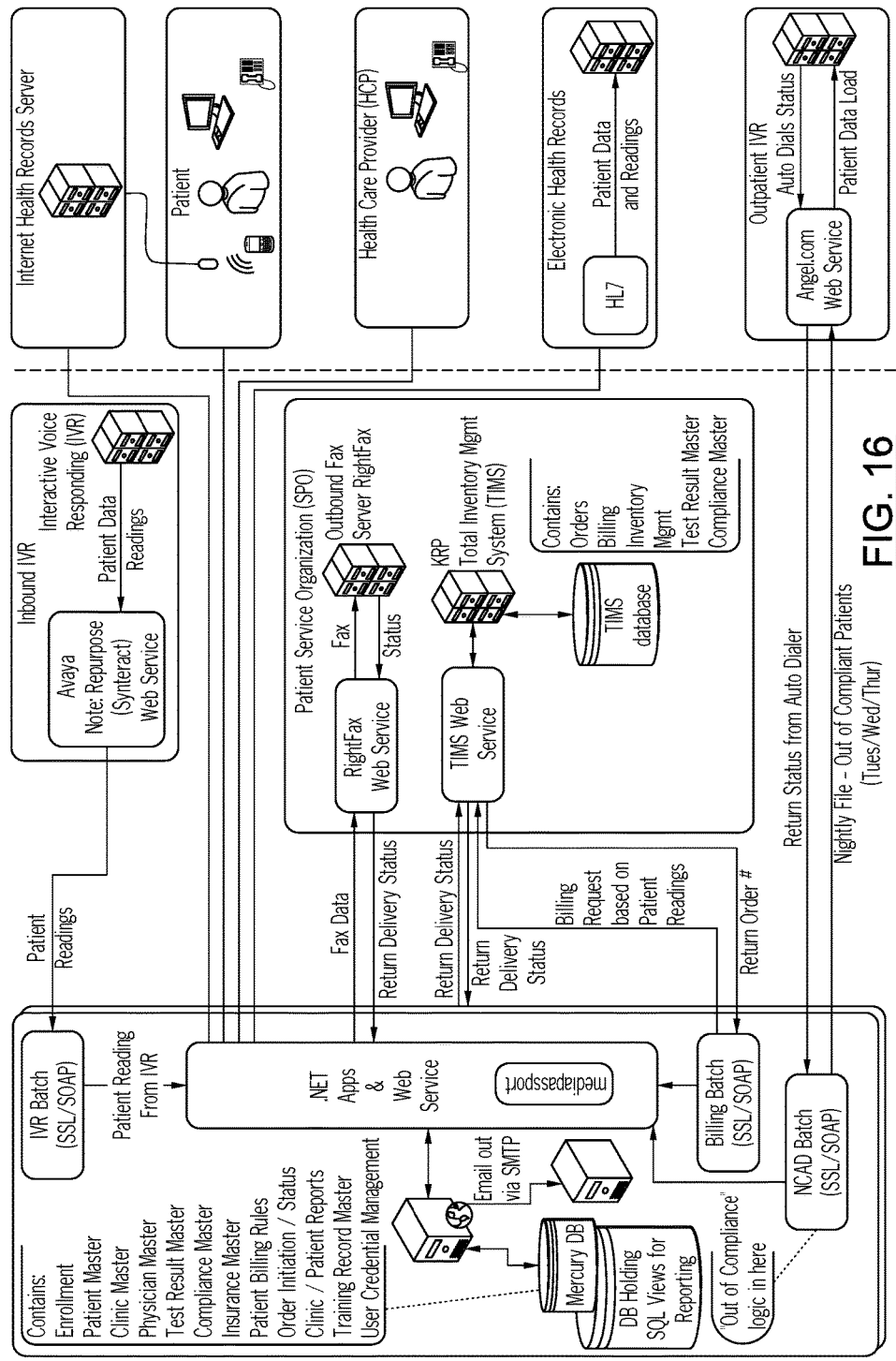
FIG. 16 is a system diagram for an example independent diagnostic testing facility patient services organization.

In some embodiments, the medical test device 10 and/or the communication hub 140 can be configured to communicate test results to an Independent Diagnostic Testing Facility (IDFT) Patient Services Organization (PSO), like are shown in FIG. 16. Presently operating IDTF PSOs include, for example, CoaguChek® Patient Services (provided by Roche Health Solutions Inc.), mdINR (a Lincare Company), and Alere Home Monitoring, Inc. Test results can be communicated by the user to the IDTF PSO, e.g., by phoning in the results or entering the result directly in the IDTF PSO Internet portal. Test results can also be communicated semi-automatically or automatically to an IDTF PSO by connecting the medical test device 10 to a computing device using an accessory such as, for example, the CoaguChek® XS Connect (Roche Diagnostics), or a cellular access communication hub, such as the Alere™ MobileLink (Alere) or 2Net™ Hub (Qualcomm Life) cellular gateway. For more information, reference may be made to Jones, Jay, "Chapter 20 Integration of Point-of-Care Testing into Regional Healthcare Networks." *Point-of-Care Testing: Needs, Opportunity, and Innovation* 3$^{rd}$ *Edition*. Eds. Christopher Price, Andrew St John and Larry Kricka. AACC Press, 2010. Additionally, the CoaguChek® Link Quick Reference Guide (2013) provides clinicians and patients on warfarin therapy with the convenience of a single, secure and easy-to-use website for managing PT/INR testing. See CoaguChek® Link Healthcare Professional's Manual (2013) and CoaguChek® Link User's Manual (2013) (Roche Diagnostics).

IDTF PSOs can operate in a wide range of sequences and actions, and the following scenarios are presented to describe some of the functions of the IDTF PSO. Operation typically begins with a patient manually entering their test results on an internet web site or phoning their tests results in using an automated or operator assisted inbound Interactive Voice Response (IVR) system. Healthcare providers can also enter the patients test results using the internet into the IDTF PSO. Once the patient's test results are entered, the results are visible to the patient, healthcare provider, and the IDTF PSO. The test results are evaluated by the IDTF computer system according to HCP/clinic preferences for a notification range. If the test results are within the notification range, an IDTF PSO clinician will phone the patient's healthcare provider and provide an oral notification that the test results are within the notification range, and a facsimile notification will be sent automatically from the IDTF PSO to the HCP. If the test results are not within the notification range, the IDTF PSO automatically sends a facsimile to the healthcare provider notifying the healthcare provider that the patient has performed a test. An outbound Interactive Voice Response (IVR) system, such as Genesys® Angel, notifies patients that are non-compliant in the frequency of their testing such as with a phone call on Tuesdays and Thursdays to remind the patient to test. The outbound IVR receives confirmation on whether the call was received by human voice or voice mail.

IDTF billing identifies billable events based upon billing rules associated with the patient's insurance policy. Billable events not reimbursed by insurance are termed overages that patient has the direct responsibility to pay. The billing events are transferred to the Total Inventory Management System (TIMS) for claims processing with insurance companies and patients. The total inventory management system also permits patients to order consumables such as test strips and lancets on the IDTF internet portal. Other known functions and services may also be provided by the IDTF PSO.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality. It is understood that grouping of operations within in a given module is not limiting and operations may be shared amongst multiple modules or combined into a single module.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways.

What is claimed is:

1. A communication interface apparatus for use with a handheld medical test device having an infrared transmitter, comprising:
   an attachment member providing an enclosure and configured to detachably couple to a housing of the medical test device, where the attachment member substantially overlays a rear side of the medical test device;
   an infrared receiver residing in the enclosure and configured to receive data wirelessly in accordance with a first communication protocol from the infrared transmitter of the medical test device, where an input port of the infrared receiver aligns with an output port of the infrared transmitter in the medical test device when the attachment member is coupled to the medical test device;

a secondary transceiver residing in the enclosure and configured to transmit data wirelessly in accordance with a second communication protocol, where the first communication protocol differs from the second communication protocol;

a controller residing in the enclosure and that operates in a low power mode, wherein the controller is configured to periodically transition from the low power mode to a normal mode, and interacts with the infrared receiver in the normal mode to receive data from the medical test device, where the communication interface apparatus consumes more electric power in the normal mode than the low power mode; and a power source residing in the enclosure and interfaced with the controller, wherein the attachment member has a planar body that defines a top edge, a bottom edge, two opposing side edges extending between the top edge and the bottom edge and the enclosure therein, wherein the planar body of the attachment member defines a longitudinal axis extending between the top edge and the bottom edge of the planar body and the planar body is shaped such that the longitudinal axis is parallel with a horizontal surface upon which the attachment member rests while the attachment member is coupled to the medical test device;

wherein the infrared receiver is arranged in line-of-sight with the infrared transmitter in the medical test device when the attachment member is coupled to the medical test device;

the controller is interfaced with the infrared receiver and the secondary transceiver and operable to convert data between the first and second communication protocols;

a power switch is electrically interconnected between the power source and the controller, where the power switch is actuatable by a user to selectively power on and off the communication interface apparatus;

the attachment member has two clip portions that extend outwardly from opposing side edges of the attachment member and configured to clip to an outer side surface of the medical test device, such that the attachment member overlays a rear side of the medical test device when the attachment member is coupled to the medical test device; and the attachment member has an overhang portion extending outwardly from a top edge of the attachment member and overlays a portion of a top side of the medical test device when the attachment member is coupled to the medical test device, wherein the overhang portion encases the infrared receiver and the input port of the infrared receiver faces the top side of the medical test device.

2. The communication interface apparatus of claim 1 further comprising a visual indicator residing in the overhang portion and electrically connected to the controller, wherein the visual indicator is illuminated while data is transmitted between the medical test device and the communication interface apparatus.

3. The communication interface apparatus of claim 1 wherein the secondary transceiver transmits data in accordance with IEEE 802.15 wireless communication standard.

4. The communication interface apparatus of claim 1 wherein the infrared receiver and the secondary transceiver are powered down in the low power mode and powered up in the normal mode.

5. A system comprising
a communication interface apparatus according to claim 1, and
a handheld medical test device having an infrared transmitter.

6. The system of claim 5, wherein the housing of the medical test device is formed by an upper shell and a lower shell coupled together and forms a groove where an edge of the upper shell abuts against an edge of the lower shell, and each clip portion of the attachment member of the communication interface apparatus includes a tongue that is received in the groove to create a tongue-and-groove joint when the attachment member is coupled to the medical test device.

7. A kit for interfacing with a medical test device, comprising
a communication interface apparatus of claim 1 or a system of claim 5, and
a communication hub that plugs into a AC power source and is configured to communicate data wirelessly with the secondary transceiver of the communication interface apparatus.

8. The kit of claim 7 wherein the communication interface apparatus operates in a low power mode and periodically transitions from the low power mode to a normal mode that consumes more electric power than the low power mode, wherein, upon transitioning to the normal mode, the controller interacts with the infrared receiver to query the medical test device and
wherein, upon failing to receive a response to the query from the medical test device, the communication interface apparatus transitions back to the low power mode, and
wherein, upon receiving a response to the query from the medical test device, the controller interacts with the infrared receiver to transmit a request for test results to the medical test device.

9. The kit of claim 8 wherein, in response to receiving a test result from the medical test device, the controller interacts with the secondary transceiver to transmit the test result to the communication hub.

* * * * *